United States Patent [19]

Hull

[11] 4,039,750
[45] Aug. 2, 1977

[54] AUDIO FREQUENCY PHASE MODULATOR IN HEARING TEST SYSTEM

[76] Inventor: Robert E. Hull, 2002 Woody Drive, Billings, Mont. 59102

[21] Appl. No.: 488,050

[22] Filed: July 12, 1974

[51] Int. Cl.$^2$ .......................................... H04R 29/00
[52] U.S. Cl. .................................................. 179/1 N
[58] Field of Search .................... 179/1 N, 107 S, 1 J; 332/20, 16 R; 181/.5 G, .5 J; 73/553

[56] References Cited

U.S. PATENT DOCUMENTS

| | | | |
|---|---|---|---|
| 2,489,653 | 11/1949 | Leslie | 179/1 J |
| 2,768,236 | 10/1956 | Allison | 179/1 N |
| 2,881,393 | 4/1959 | Lacy | 332/16 |
| 3,119,964 | 1/1964 | Crafts | 332/16 |
| 3,404,235 | 10/1968 | Goldberg | 179/1 N |

FOREIGN PATENT DOCUMENTS

| | | | |
|---|---|---|---|
| 493,601 | 6/1953 | Canada | 332/16 |

OTHER PUBLICATIONS

TELEERA (English Edition) (Italy), No. 20, (Mar. 1969), E. Ferrarin, pp. 5-18.

Primary Examiner—Kathleen H. Claffy
Assistant Examiner—Joseph Popek
Attorney, Agent, or Firm—David A. Veeder

[57] ABSTRACT

Disclosed is a test system primarily designed for free field testing of the hearing of an individual utilizing phase modulation to reduce or eliminate the production of standing waves thereby permitting accurate determination of pure tone hearing acuity. The test system consists of an audio signal source which may be the continuous or pulsed sine wave output of an audiometer, audio frequency signal generator, audio oscillator, or tape recorder wherein said stimulus signal is applied to a phase modulator. The phase modulator may be either an electronic or mechanical device or any combination thereof for periodically shifting the phase of the stimulus signal a predetermined amount. The phase modulated signal may be applied directly to an acoustic transducer or transducers if of sufficient amplitude or it may be amplified by an audio amplifier or amplifiers prior to such application. The subject may also be biological organisms, an animal or a material wherein the invention disclosed accomplishes a test function other than that confined to hearing.

1 Claim, 8 Drawing Figures

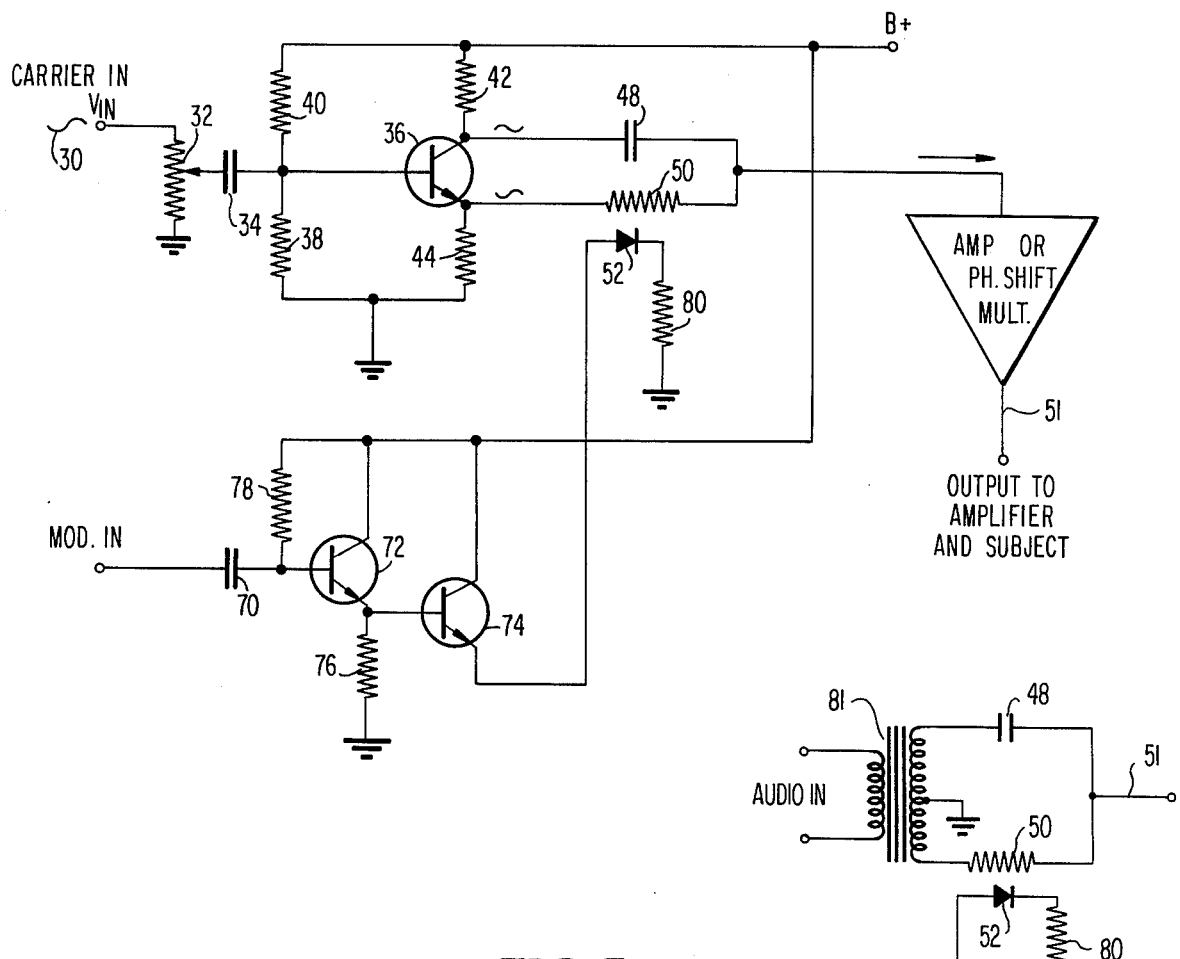
FIG. 5
FIG. 5a
FIG. 5b
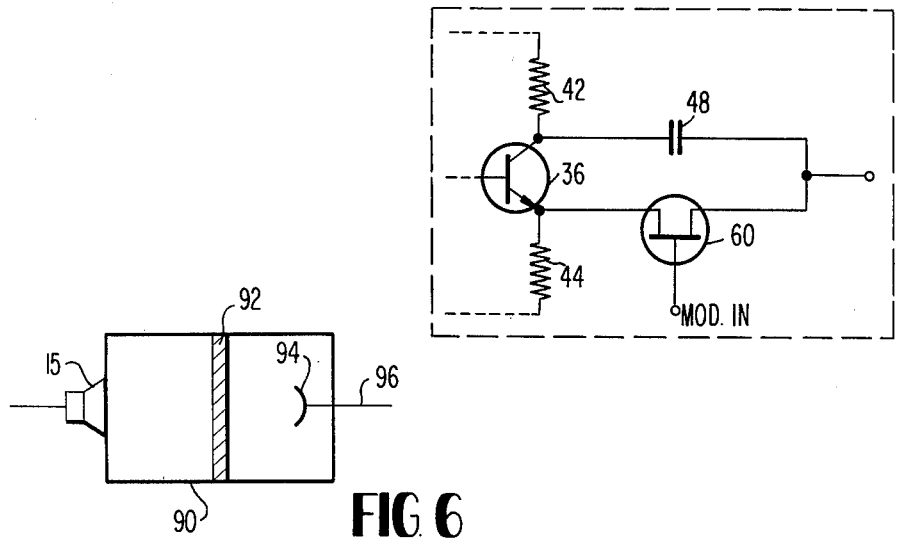
FIG. 6

AUDIO FREQUENCY PHASE MODULATOR IN HEARING TEST SYSTEM

BACKGROUND OF THE INVENTION

1. Field of the Invention

This invention primarily relates to devices for measuring the sense of hearing by free field pure tone testing. It is especially useful for the testing of infants and pre-school children; however it is not necessarily limited to such individuals. Since it is quite difficult to test the hearing of infants and pre-schoolers by the use of conventional earphones, this invention provides a means of determining the hearing threshhold level in a free field by observation of the reflex action of the subject or by the use of electronic monitoring equipment which indicates the subject's awareness of the auditory stimulus. This invention also relates to devices for stimulating biological organisms and animals or measuring the acoustical properties of materials or enclosures. It is useful in the fields of psycho-acoustics and bio-acoustics for the testing and stimulating of animals and biological organisms.

2. Description of the Prior Art

There are several different methods which have been employed in the prior art to test hearing in a free field hearing test system. One typical approach is the use of a warble tone. Allison U.S. Pat. No. 2,768,236 shows a device in which a warble tone is produced by means of frequency modulating methods designed into an audiometer which in turn energizes certain loud speakers. The effect of such a warble tone is to reduce standing waves by only about 20% thus limiting the effectiveness for free field testing. This helpful warble tone method of reduction of standing waves is present only in very expensive clinical audiometers. Goldberg U.S. Pat. No. 3,404,235 utilizes white noise or narrow band noise for the estimation of speech threshhold since such noise does not suffer from the effects of standing waves. Unfortunately, clinical hearing evaluations using such white or narrow band noise yield little useful diagnostic data for hearing evaluation purposes, due to its inherent lack of pure tone quality and resultant distortion of stimulus signal. However, one problem common to all prior art techniques is that standing wave reduction is relatively ineffective and quite expensive. It was also desired that a solution to the problem of further reduction in standing waves be found that was inexpensive and readily adapted to commercially available and commonly used audiometers without further modification. For these and other reasons, the following invention was perfected.

SUMMARY OF THE INVENTION

According to the present invention, an improved method of reducing or eliminating acoustic standing waves through the use of phase modulation rather than frequency modulation is disclosed as applied to individual hearing test systems and test systems employing subjects other than individuals. The phase modulator itself is comprised of any of a variety of electronic circuits or mechanical devices such as rotating vanes, rotating drums or rotating wheels. An audio signal source emitting a pure tone continuous or pulsed sine wave output such as is available from a conventional audiometer is applied to the phase modulator device. At the same time, the phase modulator device shifts periodically the phase of said audio signal source by means of a modulation signal source, preferably of a sub-audible frequency in the area of five cycles per second, which may be emitted by any alternating voltage or current source such as an audio oscillator. The resultant phase modulated stimulus signal, if of sufficient power, may be applied directly to an acoustical transducer or transducers. If not, the phase modulated stimulus signal may be applied to an audio amplifier or multiple audio amplifiers for amplification and then applied to the acoustical transducer or transducers.

It is an object of the present invention to provide an inexpensive, useful and efficient means of reduction or elimination of acoustic standing waves produced by a sine wave sound emitted from a transducer located in an acoustically reflective environment.

It is another object of the present invention to provide a means of reducing or eliminating acoustic standing waves produced by a sine wave sound emitted from a transducer located in an acoustically reflective environment for use in hearing test systems for individuals.

It is another object of the present invention to provide a means of reducing or eliminating acoustic standing waves produced by a sine wave sound emitted from a transducer located in an acoustically reflective environment for use in hearing test systems for individuals who are infants or pre-school children.

It is another object of the present invention to provide a means of reducing or eliminating acoustic standing waves produced by a sine wave sound emitted from a transducer located in an acoustically reflective environment for use in testing systems for biological organisms.

It is another object of the present invention to provide a means of reducing or eliminating acoustic standing waves produced by a sine wave sound emitted from a transducer located in an acoustically reflective environment for use in testing systems for animals.

It is another object of the present invention to provide a means of reducing or eliminating acoustic standing waves produced by a sine wave sound emitted from a transducer located in an acoustically reflective environment for use in testing systems for materials and enclosures.

The subject matter I regard as my invention is particularly pointed out and distinctly claimed in the concluding portion of this specification. This invention, together with further advantages and objects thereof, may best be understood by reference to the following description taken in connection with the accompanying drawings wherein the reference character refers to like elements.

FIGS. 5 and 5a and 5b are schematic diagrams of the invention wherein phase modulation is obtained electronically; and FIG. 6 is a schematic diagram of the invention wherein another electronic means of phase modulation is shown.

When sine wave audio signals are radiated and if the surrounding environment is not purely resistive (i.e. absorption coefficient of 100%,) reflected signals are produced which may be out of phase with the directly related signal. The algebraic additions of these out-of-phase signals produce standing waves causing a series of maximums and minimums in the sound pressure field. This has the effect of producing ambiguous results when attempting to measure the energy gradient of the directly radiated signal. By continuously changing the phase of the directly radiated signal the standing waves continually change their position within the sound field to thereby average the maximums and minimums and produce a substantially or completely homogeneous energy gradient that is measurable and predictable. The process of varying the phase of a signal is called phase modulation.

Figure 1:
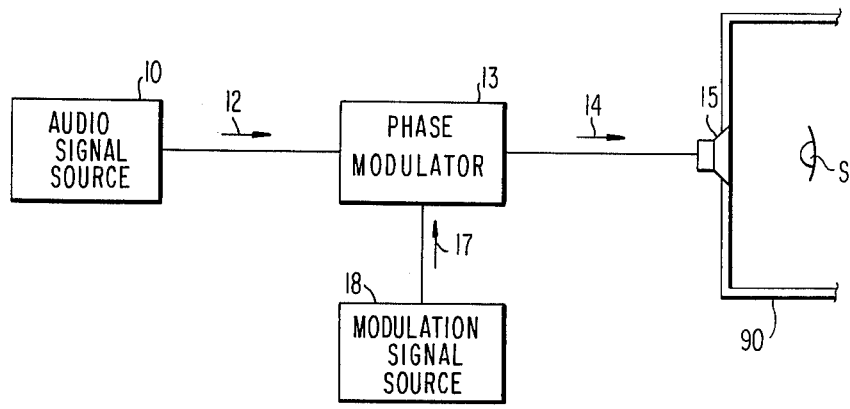
FIG. 1 is a block diagram of the components of this invention.

FIG. 1 is a schematic block diagram of one form of the invention. In FIG. 1 the audio signal source 10 sends its output 12 to a phase modulator 13. The output 14 of phase modulator 13 is sent to an acoustic transducer 15. The phase modulator 13 periodically shifts the phase of the output signal from the audio signal source some amount of degrees from 0° to 360° or a multiple thereof. The amount of the phase shift is proportional to modulation signal 17 produced by a modulation signal source 18. The modulation signal 17 can be in the form of an alternating voltage or current.

Figure 2:
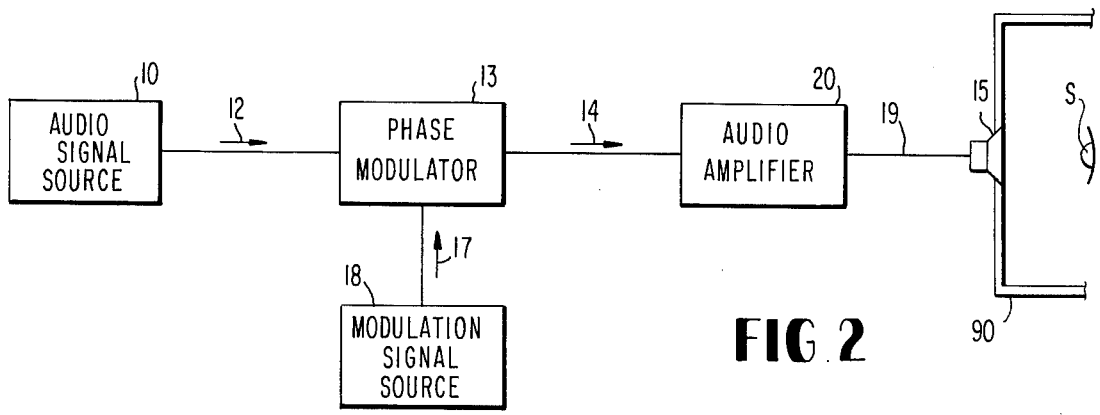
FIG. 2 is a block diagram similar to FIG. 1 wherein an amplifier has been added prior to the output stage.

As seen in the block schematic of FIG. 2, the phase modulated stimulus signal 14, if necessary, can be amplified by an audio amplifier 20 disposed between phase modulator 13 and the acoustic transducer 15. The audio signal source 12 from unit 10 can be an audio oscillator, a tape recorder player, audio signal generator or a conventional audiometer.

Figure 3:
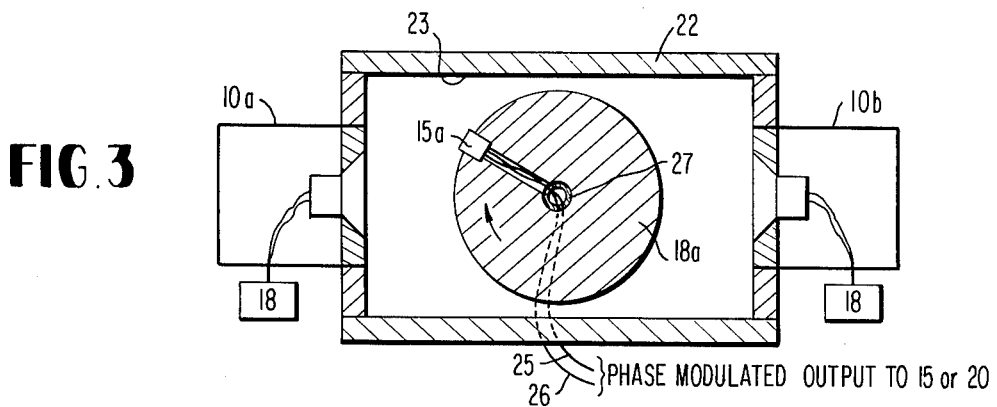
FIG. 3 is a cross-sectional diagrammatic view of the invention wherein phase modulation is obtained mechanically by virtue of a rotating drum.
Figure 4:
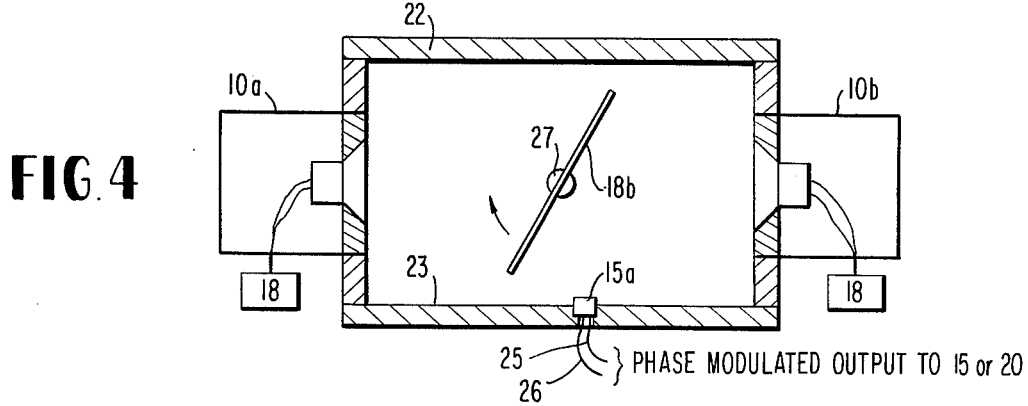
FIG. 4 is a cross-sectional diagrammatic view showing an embodiment of the invention wherein phase modulation is obtained mechanically by virtue of a rotating baffle.

In FIGS. 3 and 4, respectively, there are shown two mechanical means of obtaining phase modulation. In the embodiment of FIG. 3, speakers 10a and 10b are shown which transmit audio signals 180° out of phase to an enclosure 22 which may have a sound-absorbing interior surface 23. Within the enclosure is a rotating drum 18a which carries a microphone 15a. The rotation of drum 18a, at perhaps 5Hz, causes a phase modulated output signal to lines 25 and 26.

The embodiment of FIG. 4 is much like that of FIG. 3 except that a rotating baffle 18b is utilized to phase the audio signals from speakers 10a and 10b. The axle 27 carrying the drum 18a or the baffle 18b can be driven by a small electric motor (not shown).

As seen in FIG. 5, and as mentioned hereinabove, phase modulation can also be obtained electronically. An audio frequency carrier signal 30 is applied to variable resistor 32 and is coupled by capacitor 34 to the base of phase splitter transistor 36. The bias of transistor 36 is established by resistors 38 and 40. Load resistors 42 and 44 are approximately equal in resistance and produce substantially equal peak-to-peak voltages 180 degrees out of phase with each other. Since the total voltage gain of the circuit cannot exceed unity (when resistors 42 and 44 are of equal value) the peak-to-peak voltages at the collector and emitter of transistor 36 will be somewhat less than signal 30.

A capacitor 48, an LDR (light derived resistance) 50 and an LED (light emitting diode) 52 form the active elements of phase modulation.

The amount of phase shift produced by capacitor 48 and the resistance 50 in degrees is determined by is twice the angle whose tangent is the reactance of capacitor 48 divided by the resistance of resistor 50. Therefore, if the reactance of capacitor 48 equals the resistance of the resistor 50, the phase shift is 90 degrees (Reactance of 48 = (1/2 $\pi$ fC)).

If the resistance 50 is varied from 0 to infinity, a phase shift of from 0° to 180° is possible. If the output load impedance is maintained at a reasonably high value, the amplitude variation of the output will be negligible as the phase is shifted from 0° to 180°. If the output signal is applied to a second identical stage, the phase relationship can be shifted through a 360° range.

The phase shift (TAN = Capacitance of 48/Resistance of 50) can also be obtained by varying the capacitance of 48 or resistance 50 can be replaced by any form of variable resistance as in FIG. 5a. In FIG. 5a, the variable resistance is provided by a field effect transistor (FET) 60. By varying the gate voltage, the source to drain resistance can be varied over a large range.

Returning to FIG. 5, it can be seen that a modulation voltage or current is coupled through capacitor 70 to the base of buffer transistor 72. Here, the purpose of the buffer stage is to insure the isolation of drive transistor 74 from the modulation source. Driver transistor 74 is provided with sufficient current gain to operate the light-emitting diode 52 in series with the emitter of transistor 74. The resistor 80 provides current limiting so as to protect diode 52 from excessive currents. Resistor 80 can be replaced by an additional light-emitting diode (not shown) to operate a second stage phase shift multiplier. The intensity of the light produced by diode 52 is directly proportional to the amplitude of the modulation voltage or current. The diode 52 is mounted in close proximity to the light derived resistance 50 and is also directly proportional to the instantaneous amplitude of the modulation signal and, therefore, an instantaneous phase shift is directly (or inversely) proportional to the modulation signal.

In FIG. 5b, a second simpler method of electronic means of phase modulation is shown. In can be seen that the phase splitter transistor 36 shown in FIGS. 5 and 5a and its associated circuitry is replaced with a transformer 81. The functions of capacitor 48, resister 50, and diode 52 remain the same as in FIGS. 5 and 5a in this second electronic means.

In the above embodiments, the subject S is located in the enclosure 90 in proximity to the acoustic transducer 15. It should be understood, of course, that such enclosures are normal but not necessary. FIG. 6 discloses a material 92 being tested. A microphone pick-up 94 sends its output 96 for analysis of the sound-absorbing qualities of material 92.

In a general manner, while there have been disclosed effective and efficient embodiments of the invention, it should be well understood that the invention is not limited to such embodiments, as there might be changes made in the arrangement, disposition and form of the parts without departing from the principle of the present invention as comprehended within the scope of the accompanying claims.

I claim:

1. In combination, a sound-absorbing enclosure, and a device for reducing or eliminating standing waves produced in response to an audio signal directed to a subject located in the sound-absorbing enclosure, said device comprising, acoustical transducer means, having an input for receiving an audio input signal, for generating an acoustical output responsive to the input signal thereto, an apparatus for producing an electrical audio signal,
a phase modulation means for receiving said audio signal and modulating the same so as to produce an output signal of varying phase and of constant amplitude in reference to said audio signal, and
means for connecting said modulated output signal to the input of said acoustical transducer means to reduce the standing waves associated with the acoustical output signal generated by said acoustical transducer means, said audio signal producing apparatus comprising speaker means and said phase modulating means comprising a rotating drum, and a microphone mounted on said drum for rotation therewith, said speaker means comprising at least two speakers mounted in a wall of a housing and connected so as to differ in phase by 180° and said rotating drum being mounted within said housing.

* * * * *